US011925336B2

(12) United States Patent
Stack et al.

(10) Patent No.: US 11,925,336 B2
(45) Date of Patent: *Mar. 12, 2024

(54) GUIDEWIRELESS TRANSSEPTAL DELIVERY SYSTEM AND METHOD

(71) Applicant: Synecor LLC, Durham, NC (US)

(72) Inventors: Richard S Stack, Durham, NC (US); William L Athas, Durham, NC (US); Kevin W Johnson, Durham, NC (US)

(73) Assignee: Synecor LLC, Durham, NC (US)

( * ) Notice: Subject to any disclaimer, the term of this patent is extended or adjusted under 35 U.S.C. 154(b) by 104 days.

This patent is subject to a terminal disclaimer.

(21) Appl. No.: 17/188,936

(22) Filed: Mar. 1, 2021

(65) Prior Publication Data
US 2021/0177389 A1    Jun. 17, 2021

Related U.S. Application Data

(63) Continuation of application No. 16/396,677, filed on Apr. 27, 2019, now Pat. No. 10,959,713, which is a (Continued)

(51) Int. Cl.
A61B 17/00    (2006.01)
A61M 25/00    (2006.01)
(Continued)

(52) U.S. Cl.
CPC ... *A61B 17/00234* (2013.01); *A61M 25/0147* (2013.01); *A61M 25/10* (2013.01);
(Continued)

(58) Field of Classification Search
CPC .... A61B 17/00234; A61B 2017/00243; A61B 2017/00323; A61F 2/2427; A61F 2/2433;
(Continued)

(56) References Cited

U.S. PATENT DOCUMENTS 5,190,050 A    3/1993 Nitzsche
5,873,842 A    2/1999 Brennen et al.
(Continued)

FOREIGN PATENT DOCUMENTS

EP    1534374 B1    1/2007
EP    1807143 A1    7/2007
(Continued)

OTHER PUBLICATIONS

Sondergaard, Lars et al., First-in-Human Case of Transfemoral CardiAQ Mitral Valve Implantation, Circ. Cardiovasc Interv. 2015, 10 pages.

(Continued)

*Primary Examiner* — Kelly J Bekker
*Assistant Examiner* — Andrew P. Restaino

(57) ABSTRACT

A system and method used to deliver a valve delivery system carrying a valve to a target valve annulus in the heart includes a cable percutaneously introduced into a vasculature of a patient and positioned to run from a femoral vein, transseptally through the heart, to a femoral artery. The valve delivery system device is passed over an end of the cable at the arterial side and is secured to the cable. The valve delivery system device is pushed in a distal direction while the venous end of the cable is pulled in the proximal direction, to advance the valve delivery system to the target valve annulus. A left ventricle redirector positionable on the cable from the venous end has a distal end actively steered during advancement and positioning of the valve delivery device, exerting forces that steer the distal nose of the valve delivery device as it moves towards the valve annulus.

13 Claims, 9 Drawing Sheets

Related U.S. Application Data continuation of application No. PCT/US2017/062913, filed on Nov. 22, 2017.

(60) Provisional application No. 62/473,495, filed on Mar. 20, 2017, provisional application No. 62/461,788, filed on Feb. 22, 2017, provisional application No. 62/443,492, filed on Jan. 6, 2017, provisional application No. 62/425,584, filed on Nov. 22, 2016.

(51) Int. Cl.
*A61M 25/01* (2006.01)
*A61M 25/10* (2013.01)

(52) U.S. Cl.
CPC .............. *A61B 2017/00243* (2013.01); *A61B 2017/00323* (2013.01); *A61M 2025/0057* (2013.01); *A61M 2025/1079* (2013.01)

(58) Field of Classification Search
CPC .. A61M 2025/0057; A61M 2025/1079; A61M 25/0147; A61M 25/10
See application file for complete search history.

(56) References Cited

U.S. PATENT DOCUMENTS

| | | | |
|---|---|---|---|
| 6,004,280 | A | 12/1999 | Buck et al. |
| 6,592,581 | B2 | 7/2003 | Bowe |
| 6,613,046 | B1 | 9/2003 | Jenkins et al. |
| 7,056,314 | B1 | 6/2006 | Florio et al. |
| 7,115,134 | B2 | 10/2006 | Chambers |
| 7,481,805 | B2 | 1/2009 | Magnusson |
| 7,647,124 | B2 | 1/2010 | Williams |
| 7,729,782 | B2 | 6/2010 | Williams et al. |
| 8,096,985 | B2 | 1/2012 | Legaspi et al. |
| 8,235,916 | B2 | 8/2012 | Whiting et al. |
| 8,435,227 | B2 | 5/2013 | Takagi et al. |
| 8,606,369 | B2 | 12/2013 | Williams et al. |
| 8,827,982 | B2 | 9/2014 | Goode et al. |
| 8,926,588 | B2 | 1/2015 | Berthiaume et al. |
| 8,996,135 | B2 | 3/2015 | Elencwajg |
| 9,072,872 | B2 | 7/2015 | Asleson et al. |
| 9,078,994 | B2 | 7/2015 | Rosenman et al. |
| 9,173,646 | B2 | 11/2015 | Fabro |
| 9,220,874 | B2 | 12/2015 | Pillai et al. |
| 9,320,564 | B2 | 4/2016 | Avitall et al. |
| 9,511,205 | B2 | 12/2016 | Inoue |
| 9,616,197 | B2 | 4/2017 | Serina et al. |
| 9,814,814 | B2 | 11/2017 | Corbett et al. |
| 10,105,221 | B2 | 10/2018 | Siegel |
| 2001/0005789 | A1 | 6/2001 | Root et al. |
| 2004/0003819 | A1 | 1/2004 | St. Goar et al. |
| 2004/0127847 | A1 | 7/2004 | DuBois |
| 2006/0155158 | A1 | 7/2006 | Aboul-Hosn |
| 2006/0167535 | A1 | 7/2006 | Johnson |
| 2006/0217794 | A1 | 9/2006 | Ruiz et al. |
| 2006/0217802 | A1* | 9/2006 | Ruiz ............... A61F 2/2433 623/2.11 |
| 2007/0032850 | A1 | 2/2007 | Ruiz et al. |
| 2007/0049906 | A1 | 3/2007 | Magnusson |
| 2007/0060914 | A1 | 3/2007 | Magnusson |
| 2007/0100299 | A1 | 5/2007 | Magnusson |
| 2007/0112422 | A1 | 5/2007 | Dehdashtian |
| 2007/0156233 | A1 | 7/2007 | Kapadia et al. |
| 2007/0299403 | A1 | 12/2007 | Crowe et al. |
| 2010/0160725 | A1 | 6/2010 | Kiser et al. |
| 2010/0185172 | A1 | 7/2010 | Fabro |
| 2010/0198056 | A1 | 8/2010 | Fabro et al. |
| 2010/0198192 | A1 | 8/2010 | Serina et al. |
| 2010/0198208 | A1 | 8/2010 | Napp et al. |
| 2010/0249491 | A1 | 9/2010 | Farnan et al. |
| 2011/0022057 | A1 | 1/2011 | Eigler et al. |
| 2012/0041422 | A1 | 2/2012 | Whiting et al. |
| 2012/0101442 | A1 | 4/2012 | Legaspi et al. |
| 2012/0172656 | A1 | 7/2012 | Walters et al. |
| 2014/0107399 | A1 | 4/2014 | Spence |
| 2014/0276395 | A1 | 9/2014 | Wilson et al. |
| 2014/0276782 | A1 | 9/2014 | Paskar |
| 2014/0276904 | A1 | 9/2014 | Hanson et al. |
| 2014/0303719 | A1 | 10/2014 | Cox et al. |
| 2014/0371719 | A1 | 12/2014 | Carnevale |
| 2015/0258312 | A1 | 9/2015 | Tuseth |
| 2015/0273136 | A1 | 10/2015 | Osiev |
| 2015/0305864 | A1 | 10/2015 | Quadri et al. |
| 2015/0328382 | A1 | 11/2015 | Corbett et al. |
| 2016/0066993 | A1 | 3/2016 | Avitall et al. |
| 2016/0074623 | A1 | 3/2016 | Pillai et al. |
| 2016/0158506 | A1 | 6/2016 | Eliasen et al. |
| 2016/0213472 | A1 | 7/2016 | Kim |
| 2016/0220785 | A1 | 8/2016 | Fabro |
| 2016/0317288 | A1 | 11/2016 | Rogers et al. |
| 2016/0317289 | A1 | 11/2016 | Tozzi |
| 2017/0224483 | A1 | 8/2017 | Kizuka |
| 2017/0245988 | A1 | 8/2017 | Siegel et al. |
| 2017/0258614 | A1 | 9/2017 | Griffin |
| 2017/0361065 | A1 | 12/2017 | Legaspi et al. |
| 2018/0043132 | A1 | 2/2018 | Serina et al. |
| 2018/0078370 | A1 | 3/2018 | Kovalsky et al. |
| 2018/0104398 | A1 | 4/2018 | Corbett et al. |
| 2018/0311421 | A1 | 11/2018 | Tuseth et al. |
| 2018/0318079 | A1 | 11/2018 | Patel et al. |
| 2019/0117937 | A1 | 4/2019 | Humphrey et al. |
| 2019/0151614 | A1 | 5/2019 | Hsueh et al. |

FOREIGN PATENT DOCUMENTS

| | | |
|---|---|---|
| EP | 2687254 B1 | 4/2015 |
| EP | 2913080 A2 | 9/2015 |
| EP | 3142721 A1 | 3/2017 |
| EP | 3288491 A1 | 3/2018 |
| EP | 3302363 A1 | 4/2018 |
| WO | 200060995 A2 | 10/2000 |
| WO | 2005037345 A2 | 4/2005 |
| WO | 2006052651 A1 | 5/2006 |
| WO | 2007149974 A2 | 12/2007 |
| WO | 2008012914 A1 | 1/2008 |
| WO | 2009137712 A1 | 11/2009 |
| WO | 2010085456 A1 | 7/2010 |
| WO | 2010085457 A1 | 7/2010 |
| WO | 2012178115 A2 | 12/2012 |
| WO | 2013181397 A1 | 12/2013 |
| WO | 2014065714 A2 | 5/2014 |
| WO | 2014138482 A1 | 9/2014 |
| WO | 2014197962 A1 | 12/2014 |
| WO | 2015175718 A1 | 11/2015 |
| WO | 2016176409 A1 | 11/2016 |
| WO | 2016196933 A1 | 12/2016 |
| WO | 2017139246 A1 | 8/2017 |
| WO | 2017155892 A1 | 9/2017 |
| WO | 1994003227 A1 | 4/2018 |
| WO | 2019055154 A2 | 3/2019 |

OTHER PUBLICATIONS

International Search Report and Written Opinion for corresponding PCT/US2017/062913 dated Feb. 8, 2018, 7 pages.

International Search Report and Written Opinion for PCT/US2020/017370 dated Nov. 6, 2020, 11 pages.

Supplemental European Examination Report for European Patent Applicaction No. 17874335.7, corresponding to PCT/US2017/062913, dated Jul. 9, 2020, 21 pages.

Translation of Office Action for Japanese Patent Application 2019-547598, corresponding to PCT/US2017/062913, dated Oct. 29, 2021, 4 pages.

\* cited by examiner

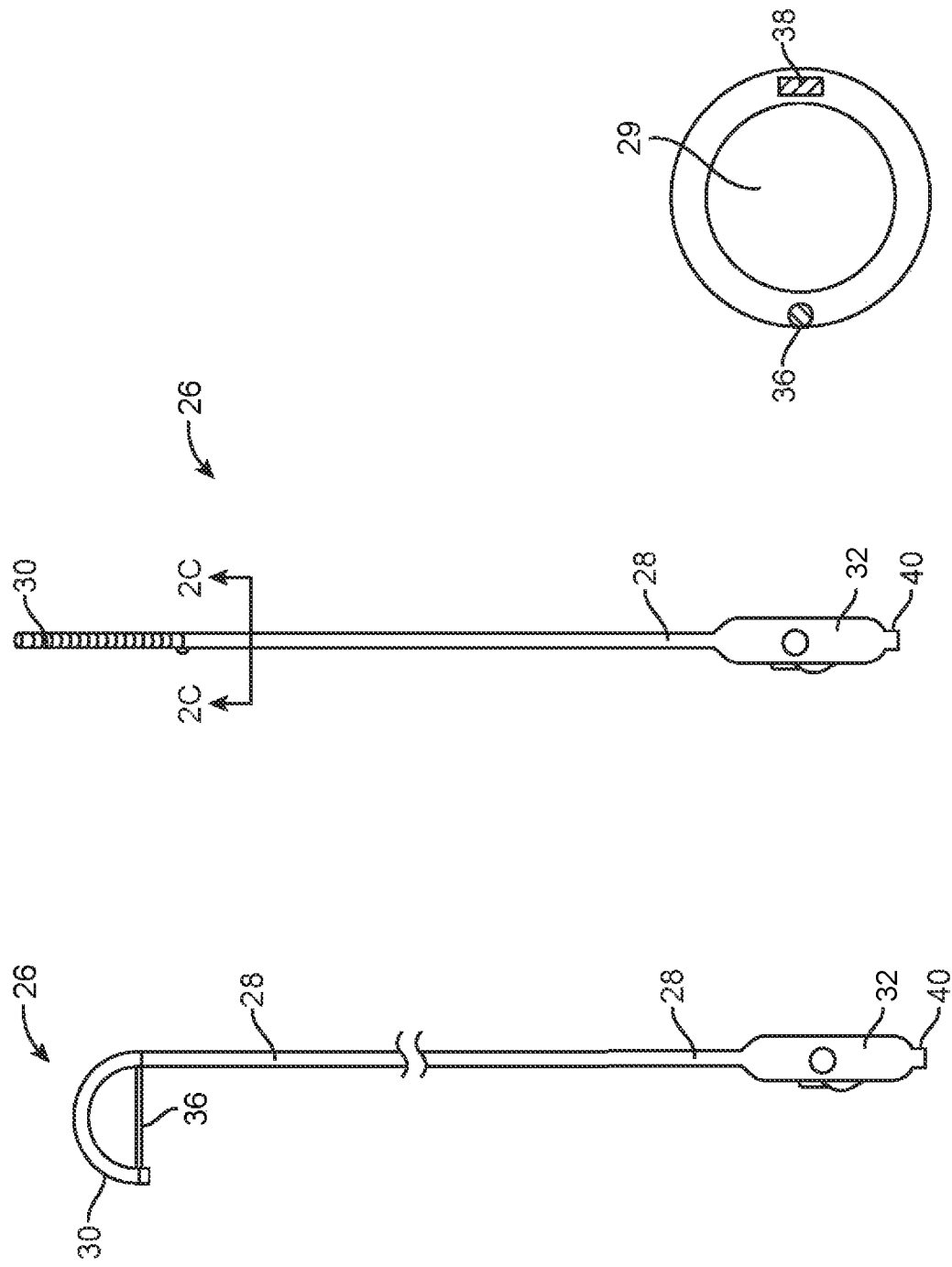

GUIDEWIRELESS TRANSSEPTAL DELIVERY SYSTEM AND METHOD

This application is a continuation of U.S. application Ser. No. 16/396,677, filed Apr. 27, 2019, which is a continuation of PCT/US2017/62913, filed Nov. 22, 2017, which claims the benefit of the following U.S. Provisional Applications: U.S. 62/425,584, filed Nov. 22, 2016, U.S. 62/443,492, filed Jan. 6, 2017, U.S. 62/461,788, filed Feb. 21, 2017, and U.S. 62/473495, filed Mar. 20, 2017.

BACKGROUND

Considerable attention has been directed towards attempting to replace or repair mitral valves using transvascular techniques. More than 40 such novel mitral valve therapeutic devices (MVTDs) that are intended to be delivered using transvascular interventional techniques have been described at this time. Many MVTDs are delivery devices for use in delivering a mitral valve prosthesis. In order for these devices to be considered minimally invasive, interventional cardiology based procedures, they must cross from the right side of the heart to the left side across the inter-atrial septum in a well-established technique known as transseptal catheterization. Because of the size and odd shape of the mitral valve carried by the replacement MVTDs, this route has proven to be extremely difficult.

All current transseptal mitral valve delivery systems rely on the traditional interventional approach that requires that these large devices be pushed over a 0.035 in. guidewire that has been previously introduced across the interatrial septum, through the left atrium then across the mitral valve and into the left ventricle. This guidewire, used in all currently available transseptal interventional devices, provides a "rail" over which these large devices can potentially be forced into position. Unfortunately, the MVTDs generally are simply too big and too rigid to negotiate the tight bends that are required when crossing into and navigating through the left atrium. As a result, they can become "stuck" when attempting to negotiate the multiple turns required for positioning within the mitral valve ring. In some instances, physicians have attempted to force these devices over the guidewire, while using the wire and the device itself to deflect off of delicate cardiac tissues, in order to achieve proper positioning within the mitral valve ring. This use of force is best avoided to prevent damage to the cardiac tissue.

In the embodiments described in this application, guidewires are not utilized to drive movement of the MVTDs into their target position for treatment (e.g. repair or replacement) of the mitral valve. Instead, protected, coordinated and synergistic forces are used to safely position the MVTDs into place. These forces include a pulling force, a pushing force, and a steering force helping to safely advance the MVTD through the vasculature into position and properly orient it relative to the mitral valve.

Attempts have been made to facilitate guidewire delivery of MVTS's by using commercially available "snare devices" delivered retrograde from the aorta through the left ventricle and left atrium in an unprotected fashion to help direct the tips of the delivery systems. These efforts were abandoned when it was found that pulling on the MVTD with a snare resulted in pulling the snare with great force up (superiorly) and across both the aortic and mitral valve leaflets leading to simultaneous wide open insufficiency of both valves and loss of blood pressure in the patient. The disclosed system eliminates this problem, allowing maximum application of force to deliver any mitral therapeutic device safely into precise position within the mitral valve ring.

BRIEF DESCRIPTION OF THE DRAWINGS

FIG. 2A is a side elevation view of the LVR with the distal end in the curved position to deploy the protective panel.

FIG. 2B is a side elevation view of the LVR with the distal end in the straight position.

FIG. 2C is a cross-section view of the shaft of the LVR taken along the plane designated 2C-2C in FIG. 2B.

DETAILED DESCRIPTION

The presently disclosed system is designed to aid in the delivery of a MVTD to a mitral valve location. The terms "mitral valve therapeutic device" or "MVTD" used here refer to any device that may be delivered to the native mitral valve site for a therapeutic purpose. In the description that follows, the MVTD is shown as a mitral valve delivery system carrying a replacement mitral valve, but it should be understood that the system and method described may be used to deliver other types of MVTD's such as those used to repair a mitral valve.

The disclosed system and method replaces the traditional interventional guidewire approach used for MVTD delivery with a percutaneous system that allows the MVTD to be safely towed to the mitral valve site within the heart. Although the system can easily be attached to any existing MVTD via the intrinsic 0.035 in. lumen present in all such interventional devices, it eliminates the need for a guidewire with the MVTD.

As will be appreciated from a review of the more detailed discussion that follows, the cable system functions to both push the proximal end of the MVTD while simultaneously pulling on the distal nose of it with equal and coordinated force to drive the MVTD across the interatrial septum. Pulling down further on the distal nose of the MVTD using the cable provides a steering force that serves to direct the stiff, bulky MVTD into position across the interatrial septum, into the left atrium and into position for deployment in the mitral valve ring (located below the interatrial septal entry point and to the patient's left). The MVTD is further positioned precisely in the center at an angle that is perpendicular to the MV plane by use of a steering mechanism present in a unique device referred to as the LV redirector (described in detail below). In some embodiments, an electronic drive unit may be used to deliver precisely coordinated pushing and pulling forces.

In the description of system and method below, the access points for the components of the system are described as the right femoral vein for the venous access and the left femoral artery for the arterial access. However, the system and method can just as readily be used with a different combination of venous and arterial access. For example, venous access may be gained via the right femoral vein and arterial access may be gained via the right femoral artery. Alternatively, both access points may be on the left side. In yet another embodiment, venous access is gained via the left femoral vein and arterial access is gained via the right femoral artery.

System

Figure 1A:
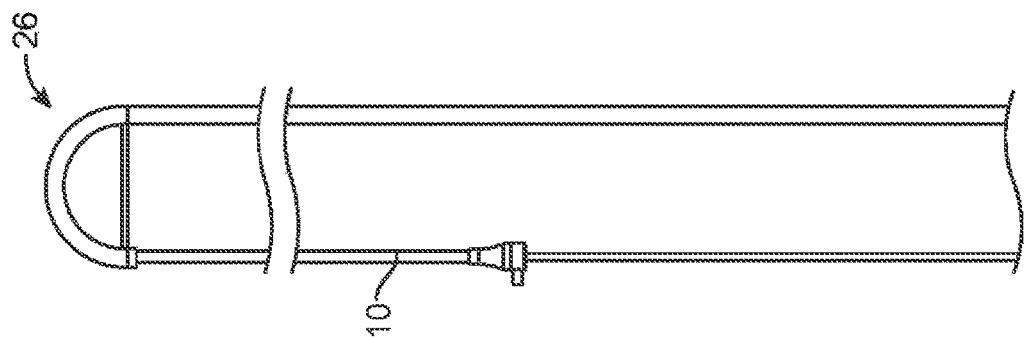
FIG. 1A is a side elevation view of a Right-to-Left conduit ("RLC") assembled with a Brockenbrough needle and dilator.

Referring to FIG. 1A, the system includes a Right-to-Left conduit 10 ("RLC"), an elongate tubular catheter having a length sufficient to permit it to extend from the right femoral vein of a human adult to the right atrium, across the interatrial septum to the left atrium, through the aorta and into the femoral artery on the patient's left or right side. The RLC 10 includes a distal portion shape set into a curved configuration to help orient the needle used for transseptal puncture towards the interatrial septum. In alternative embodiments the RLC may be steerable using pullwires or alternative means. The durometer of the RLC is relatively low (eg 55 D) as known in the art for cardiovascular catheters so as to minimize tissue trauma, although a significant length on the proximal part of the catheter is formed of a higher durometer (e.g. 70 D) to give the conduit sufficient column strength to avoid buckling when used to push during advancement of the LVR as described below. This higher durometer section may be the part of the conduit that, when the conduit fully extends between the right femoral vein and right or left femoral artery, begins at or near the proximal end of the conduit and terminates within the inferior vena, and may be as much as a third of the length of the RLC. In FIG. 1A, the RLC 10 is shown assembled with a Brockenbrough needle assembly 12 and dilator 14 for use in the transeptal catheterization step of the method.

Figure 1B:
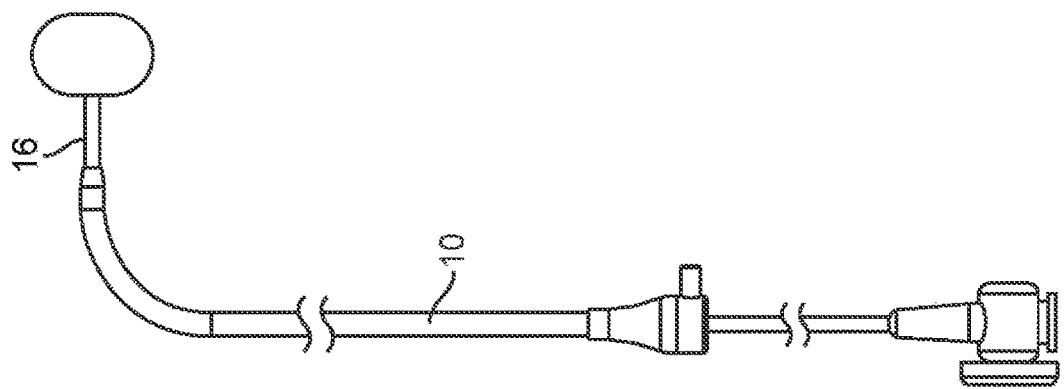
FIG. 1B is a side elevation view of the RLC of FIG. 1A assembled with a tracker balloon catheter.

The system further includes a tracker balloon catheter 16, shown extending through the RLC 10 in FIG. 1B, comprising an inflatable balloon on the distal end of the catheter. The balloon catheter 16 includes a guidewire lumen. The balloon may be inflated with a fluid or gas, including CO2 or saline, or it may be a self-expanding "vacuum balloon."

Figure 1C:
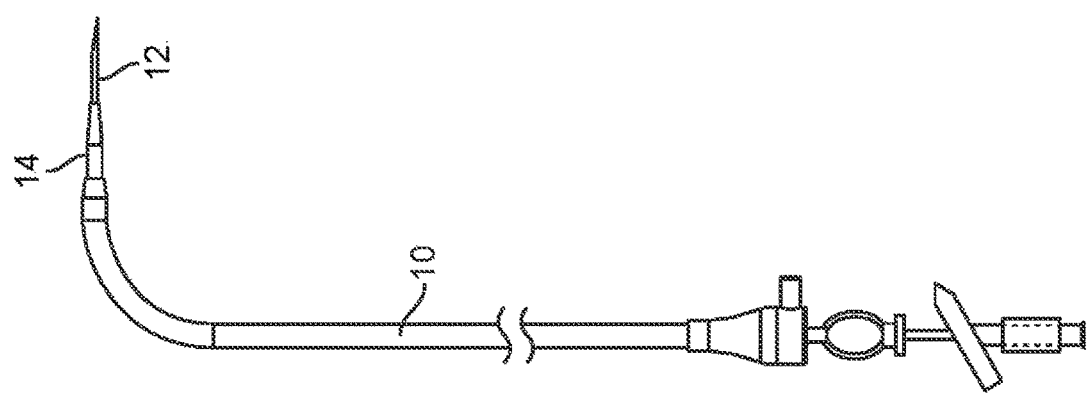
FIG. 1C is a side elevation view of the RLC of FIG. 1A assembled with a Left Ventricle Redirector ("LVR").

In FIG. 1C, the RLC 10 is shown assembled with a conveyor cable 18 and a left ventricle redirector or "LVR" 26. Details of the LVR can be seen in FIGS. 2A-2C. The LVR includes an elongate catheter shaft 28 having a proximal handle 32 with a luer port 40. As shown in the cross-section view of FIG. 2C. The shaft includes a lumen 29 accessible via the port 40. This lumen extends to the distal tip of the shaft. Incorporated within the wall of the LVR shaft are a pullwire 36 and a return wire 38. The pullwire exits the sidewall of the shaft 28 near the shaft's distal end, runs along the exterior of the shaft, and is affixed to the distal end of the shaft. Increasing tension on the pullwire 36 pulls the distal end of the shaft into a curve as shown in FIG. 2A. The handle 32 includes actuators to actuate the pull wire to bend the shaft and to actuate the return wire to return the distal end of the shaft to the generally straight configuration (as in FIG. 2B). The return wire 38 may have a rectangular diameter as shown, with the long edges oriented to aid in preferential bending of the catheter.

A membrane 30 is positioned along a portion of the distal part of the shaft and along the external portion of the pullwire 36. When the pullwire is relaxed and the shaft is in the straight configuration, the panel and pull wire run along the distal part of the shaft. The membrane forms the D-shaped barrier shown in FIG. 2A when the distal end is drawn into the curved configuration by action of the pullwire. The barrier forms a protective panel extending between the external part of the pullwire and the shaft 28, substantially eliminating gaps between the two. The panel may be made of an elastomeric polymer or other material.

Note that the term "pullwire" is not intended to mean that the pullwires must be formed of wire, as that term is used more broadly in this application to represent any sort of tendon, cable, or other elongate element the tension on which may be adjusted to change the shape of the LVR or other catheter in which the pullwire is used.

Figure 3A:
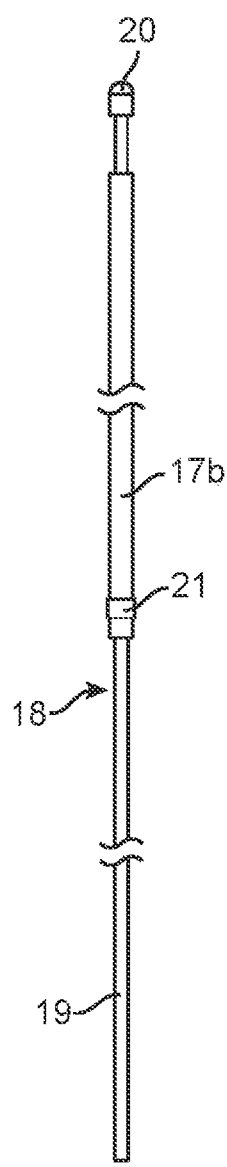
FIG. 3A is an elevation view of the cable.

The conveyor cable 18, shown in FIG. 3A comprises an elongate cable having distal cable section 17a having a broadened distal tip 20 such as the ball tip feature shown in the drawings. The tip 20 may include a distal face having convex curvature and a cylindrical proximal part with a generally flat proximal face to facilitate engagement using a snare. A larger diameter intermediate section 17b is proximal to the distal section 17a and includes a polymer coating. A proximal section 19 comprises a stiff mandrel proximal to the intermediate section 17a. The proximal section is sufficiently stiff to give column support for pushing of the cable during the RLC removal discussed below. A radiopaque marker band 21 is positioned between the proximal mandrel section 19 and the intermediate section 17b. When the cable 18 is assembled with the segmental tensioner 22 (discussed below), the soft distal tip of the segmental tensioner mates with the marker band 21, allowing the user to see on the fluoroscopic image the transition between the segmental tensioner and the intermediate (coated) section 17b of the cable.

Figure 3B:
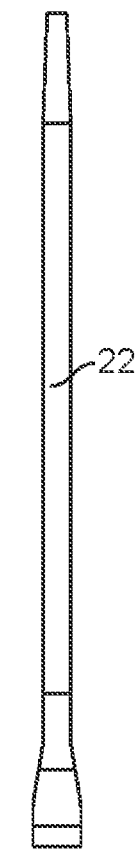
FIG. 3B is an elevation view of the tensioner.
Figure 3C:
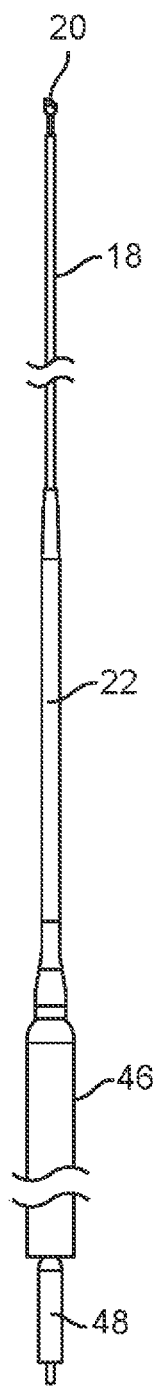
FIG. 3C shows an assembly of the cable, tensioner, MVTD and a cable lock.

Segmental tensioner 22, shown in FIG. 3B, is a short length (e.g. 30-35 mm) tubular component having a flexible tip section (e.g. 40 D) and a more rigid (e.g. 70 D) proximal hub section of broader diameter. The inner diameter of the hub section is proportioned to receive the distal tip of the MVTD. The segmental tensioner incorporates a deadstop within the shaft inner diameter to engage the polymer coated intermediate section 17b of the conveyor cable and to lock the MVTD 46 in position, preventing it from advancing independently of the conveyor cable as it is moved towards the mitral valve.

Method of Use

Figure 4A:
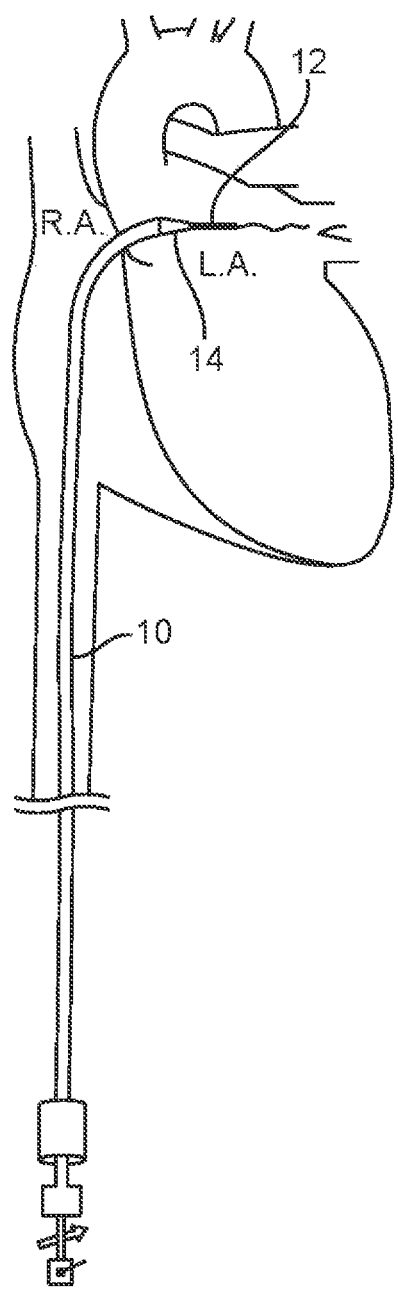
FIG. 4A schematically illustrates a section of the heart and shows the step of transseptal catheterization from the right atrium into the left atrium, using a Brockenbrough needle assembly through the RLC.
Figure 4B:
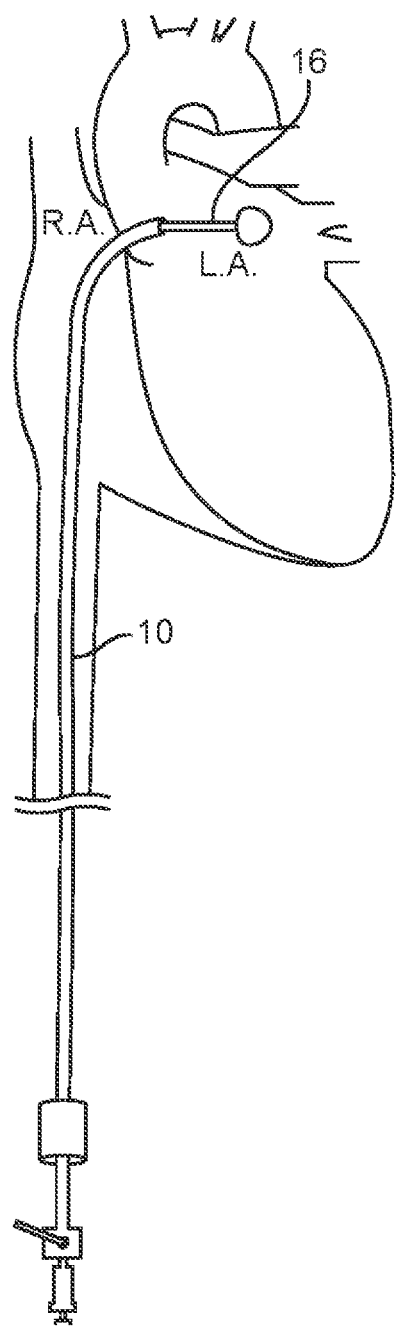
FIG. 4B is a similar view to FIG. 4A and shows the balloon catheter deployed within the left atrium.
Figure 5C:
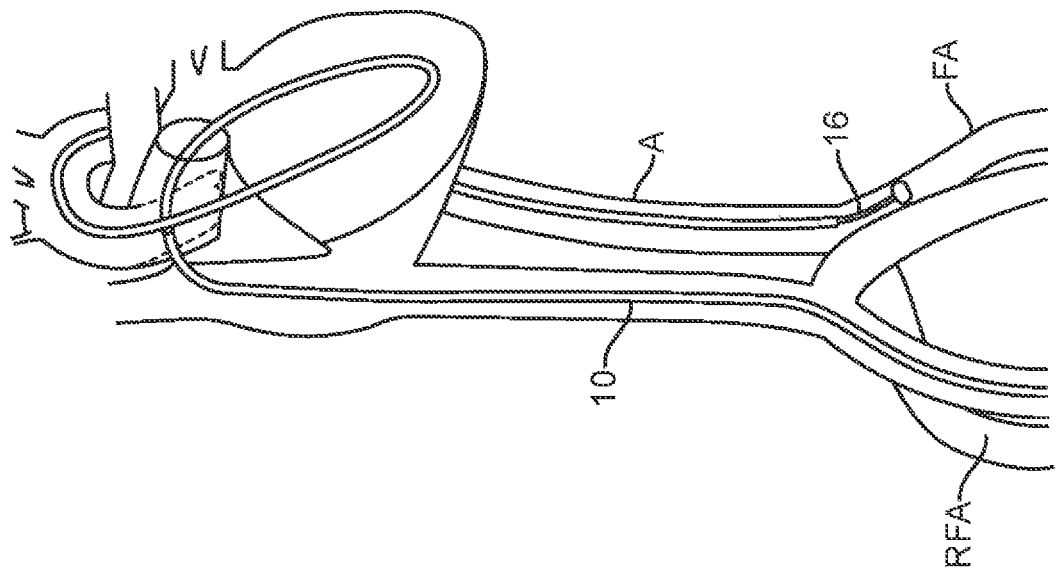
FIGS. 5A-5C are schematic illustrations of the heart depicting the left atrium, the tracker balloon being carried by the flow of blood from the left atrium, into and through the aorta, to the femoral artery.
Figure 5B:
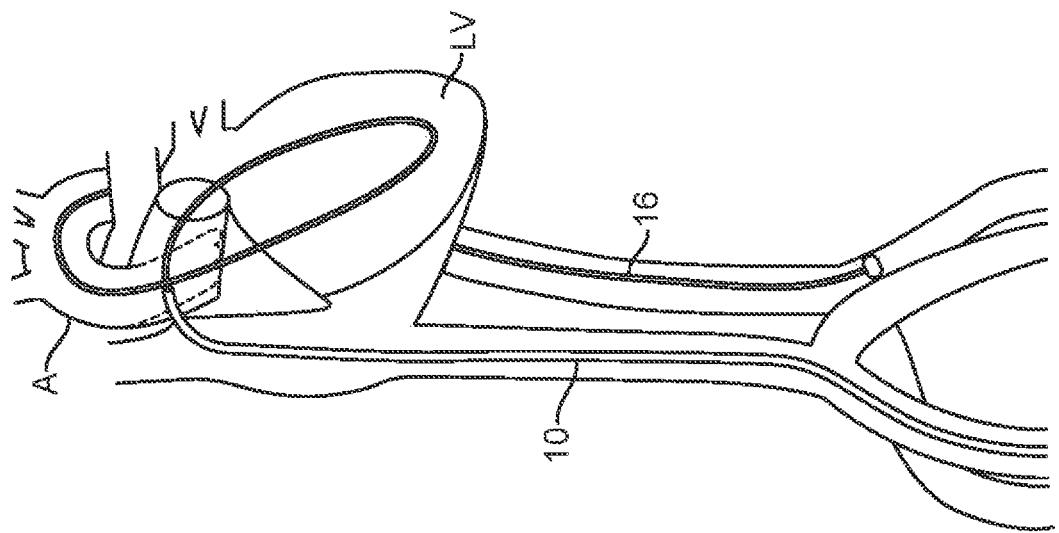
Figure 5A:
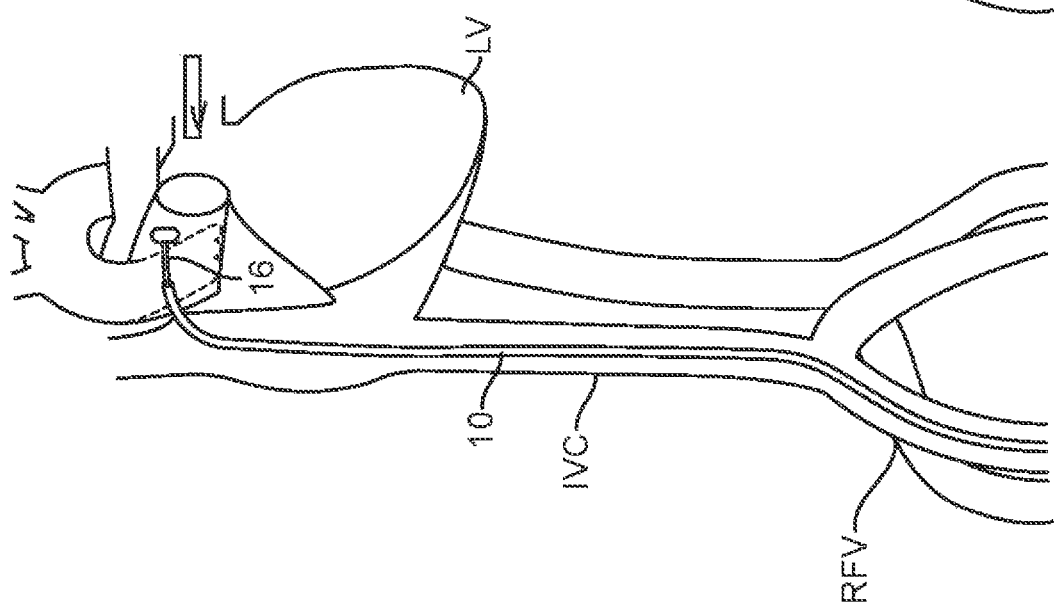

As an initial step, the RLC 10 is introduced using the well-known technique of transseptal catheterization from the right atrium (RA) into the left atrium (LA), such as by using a Brockenbrough needle assembly 12, 14 through the RLC 10, which is positioned in the right femoral vein (RFV) as shown in FIG. 4A. Once the distal end of the RLC 10 is disposed in the left atrium, the needle is withdrawn and the tracker balloon catheter 16 is passed through the RLC into the left atrium. The balloon may have a concave proximal face to increase the surface area of the balloon in the upstream direction. Once deployed within the left atrium, the flow of blood carries the tracker balloon into and through the aorta to the femoral artery as shown in FIG. 5B. As discussed previously, this description describes left side access to the arterial vasculature, but in alternative methods the tracker balloon catheter 16 may be diverted to the right femoral artery (RFA). The RLC is the advanced over the tracker balloon catheter 16 towards the left or right femoral artery. See FIG. 5C.

The tracker balloon catheter is withdrawn from the RLC, and the conveyor cable 18 is inserted into the RLC 10 on the patient's right ride and advanced. This directs the tip of the cable 18 into the left femoral artery. A snare introduced into the left femoral artery grasps the ball tip 20 of the conveyor cable as shown in FIG. 6A.

Figure 6C:
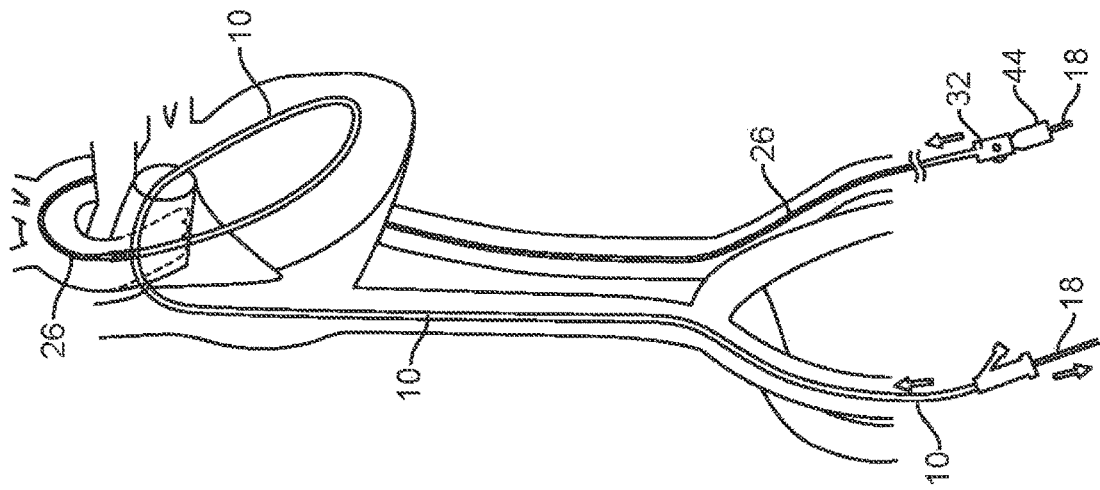
FIG. 6C illustrates the advancement of the LVR over the RLC.
Figure 6B:
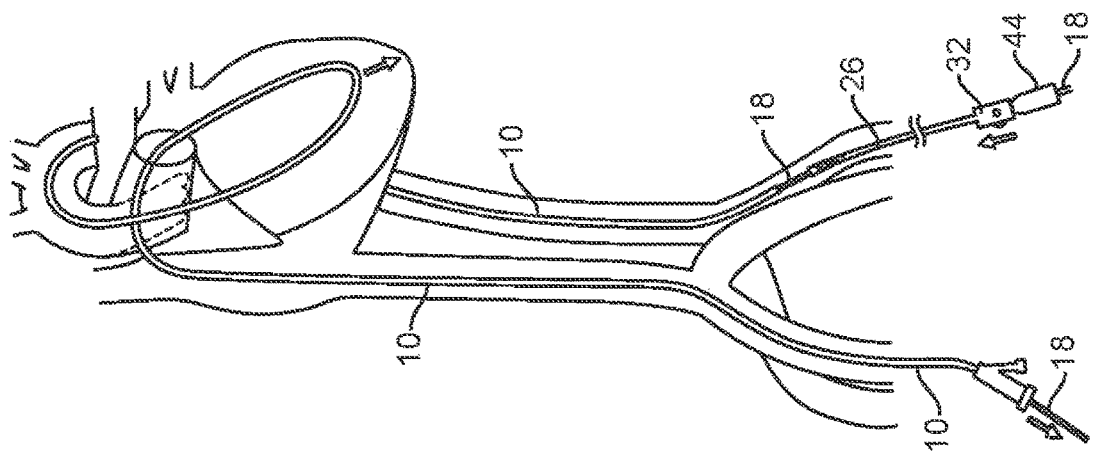
FIG. 6B illustrates the step of advancing the LVR over the cable and the locking of the LVR to the cable.
Figure 6A:
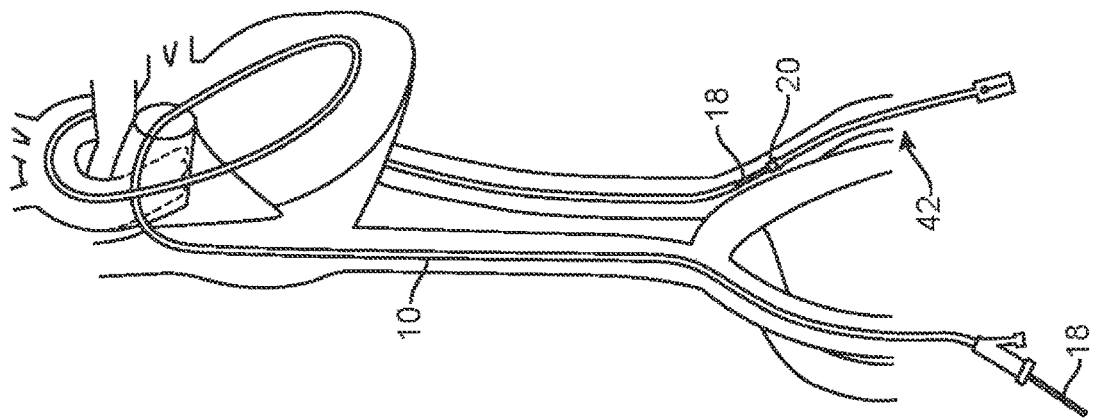
FIG. 6A shows the snaring of the ball tip of the cable in the left femoral artery after the cable been passed through the RLC.

Referring to FIG. 6B, the left ventricle redirector (LVR) 26 is introduced over the cable. The lumen of the LVR slides over the ball tip and shaft of the cable 18. The LVR is pushed towards the RLC while the RLC is pushed towards the LVR, causing the LVR to advance its distal end over the exterior surface of the RLC 10. This eliminates the exposed section of cable 18 between the LVR and RLC, and because the conveyor cable is much more flexible than the LVR or RLC, this step removes flexibility from the assembly now extending through the vasculature and heart. A cable lock 44 is used to lock the proximal end of the LVR onto the conveyor cable outside the access point to the femoral artery so that the LVR and cable will move together. The user pulls on the cable 18 on the patient's venous side (in FIG. 6B, the patient's right which is the left side of FIG. 6B). On the patient's arterial side (in FIG. 6B, the patient's left which is the right side of FIG. 6B), the user pushes the LVR 26. Note that since the LVR is locked to the conveyor cable 18, the actions of pulling the cable 18 and pushing the LVR advance the LVR into the aorta. If the system is configured such that the LVR slides over the RLC, this step is accompanied by the pushing on the RLC 10 from the venous side. Pushing the RLC during advancement of the LVR pushes the loop of the RLC into the apex of the RV as indicated by the arrow in FIG. 6B, keeping it away from delicate valve structures and chordae tendineae. If the RLC is not advanced, it may be withdrawn towards the venous access location as the LVR is advanced towards the left ventricle.

Once within the heart, the LVR is pushed strongly into the apex of the left ventricle by a pushing force applied to its proximal end.

Figure 7:
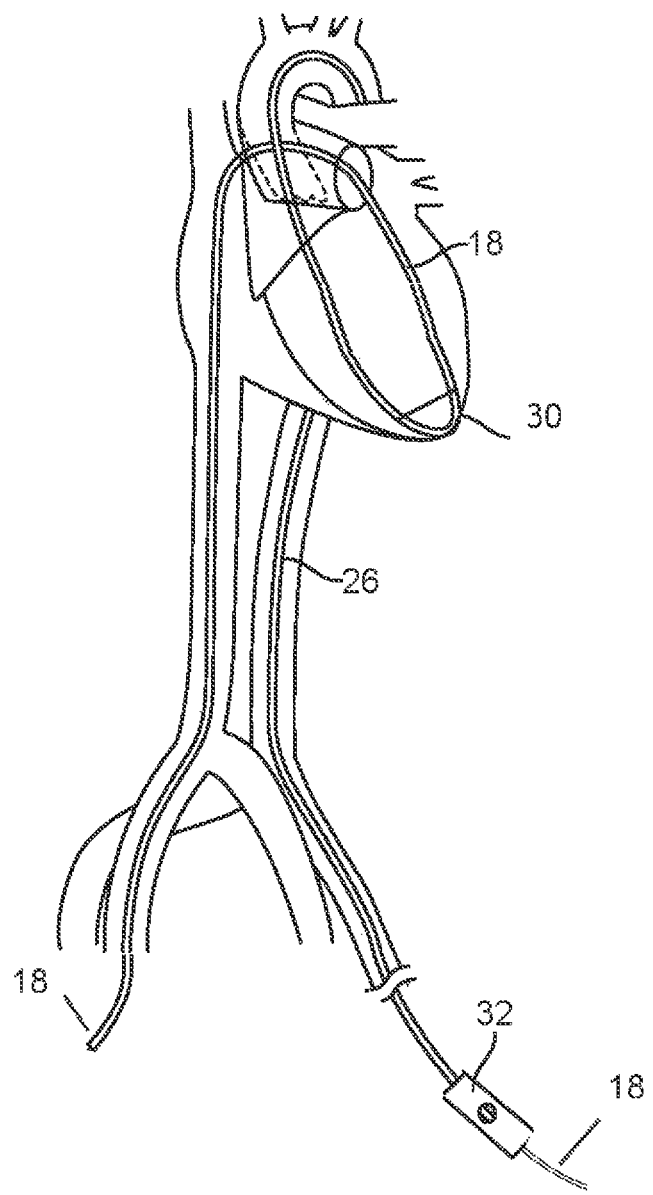
FIG. 7 shows the LVR in the expanded configuration within the left ventricle after removal of the RLC.

The RLC is next withdrawn from the venous side while a pushing force is applied to the cable on that same side. FIG. 7 shows the configuration after the RLC has been removed and the protective panel of the LVR has been deployed in the left ventricle via activation of the pullwire. The cable 18 is still in place as shown. The segmental tensioner 22 is positioned over the cable 18, followed by the MVTD, with the distal tip of the MVTD being inserted into the hub of the segmental tensioner. A cable lock 48 locks the MVTD and segmented tensioner 22 assembly onto the cable 18. The cable lock 44 locking the LVR to the cable 18 is removed.

Figure 8A:
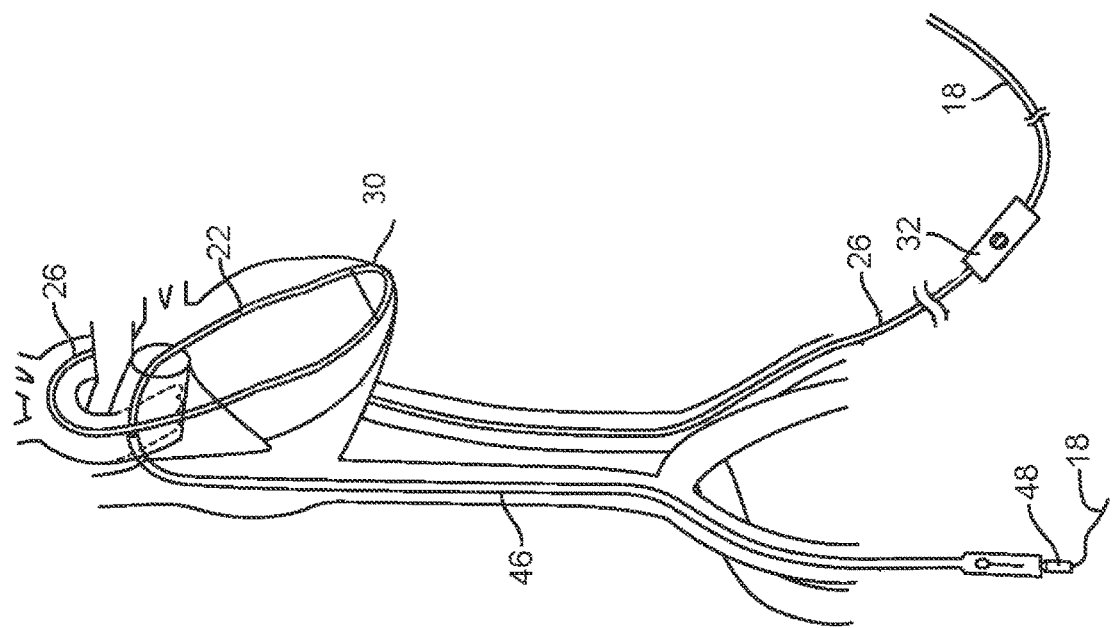
FIGS. 8A and 8B show the MVTD delivery system and tensioner on the cable being drawn by the cable across the interatrial septum towards the mitral valve ring.
Figure 8B:
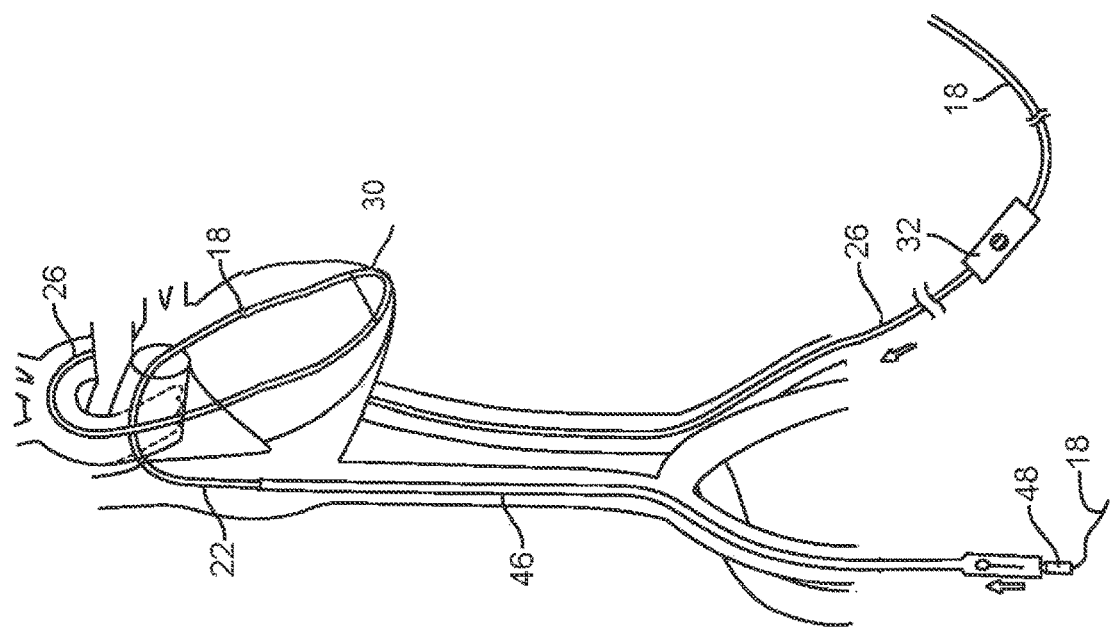

In FIG. 8B, the MVTD 46 has entered the venous circulation and is advancing toward the right atrium, led by the segmental tensioner 22, as the system is pulled by the cable while the MVTD is simultaneously pushed along at the same rate in a coordinated manner. The segmental tensioner 22 leads the way as it crosses the interatrial septum and provides a gradual transition to the bigger and stiffer MVTD (FIG. 8A).

At this point, a significant pulling force is applied to the MVTD/tensioner assembly by the cable 18. This force is slightly more than the "push force" force on the MVTD 46 so as to pull the distal nose of the MVTD down and to the patient's left through the interatrial septum. Despite the pushing force of the LVR into the apex, with ever increasing pull force, there is a strong tendency to cause the loop of the cable contained in the steerable section of the LVR to be pulled upward into the valve structures above. This tendency is overcome by the synergistic downward pushing force exerted by the segmental tensioner as it enters the lumen at the distal end of the LVR in the LV apex (FIG. 8B). It ensures that the cable 18 is positioned away from the aortic and mitral valve leaflets and chordae tendineae by maintaining the cable 18 safely away from the valve structures within the LVR's protective sleeve.

In addition to the importance of maintaining the cable 18 loop in the apex of the ventricle, another key function of the LVR is to aid in the final steering of the MVTD into the center of the mitral valve ring at an angle that is perpendicular to the mitral valve ring plane. The user fine tunes the MVTD position within the ring through a combination of adjustments to pull wire tension, torqueing of the LVR, and push-pull of the LVR from the handle.

Figure 9A:
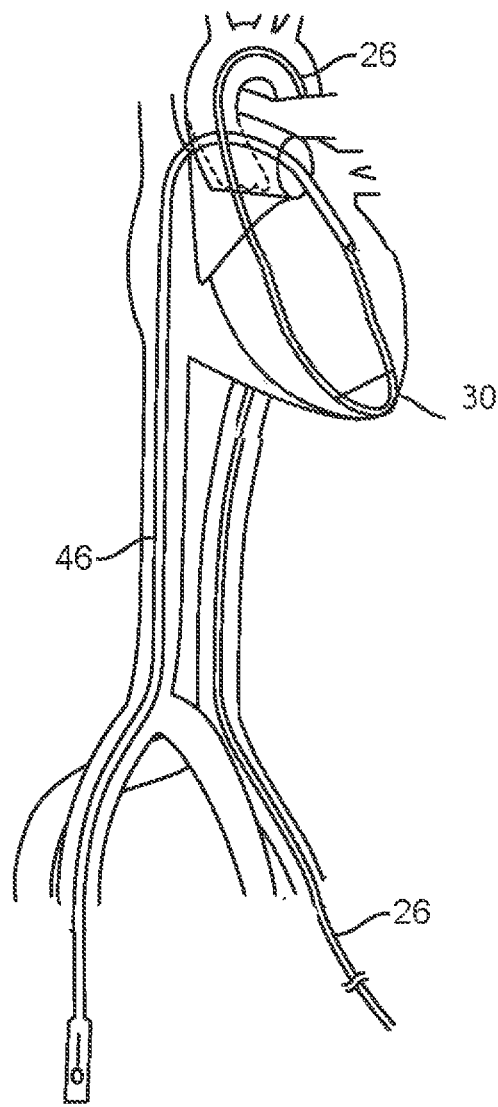
FIG. 9A shows the MVTD delivery system positioned at the mitral valve as the MVTD is being centered within the valve.
Figure 9B:
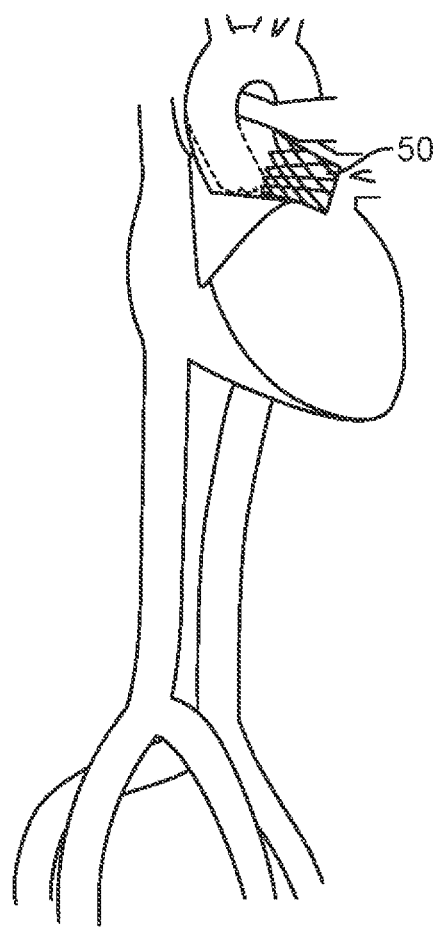
FIG. 9B shows the mitral valve in place at the mitral valve ring MVTD following deployment from the MVTD.

FIG. 9A shows the MVTD delivery system in place and centered in the mitral valve ring. After deployment of the mitral valve from the mitral valve delivery device, the arterial side of the cable is disconnected and withdrawn through the LVR as the mitral valve delivery device is withdrawn out of the body through the venous sheath. Finally, the LVR is withdrawn from the arterial sheath and the replacement valve alone remains in place (FIG. 9B).

It can be appreciated that an automated alternative to the manual method and system described above is conceivable and within the scope of this disclosure. Such a system would include drive elements that engage and selectively push/pull the instruments at the venous side, and drive elements that engage and selectively push/pull the instrument at the arterial side. In such an embodiment, the MVTD and cable are attached to a drive unit (which may be table mounted) after connection of the MVTD and deployment of the LVR, just before the MVTD is set to enter the venous sheath. The drive unit may be one configured to allow the cable 18 to be set between rollers that will cause a pulling force to be applied to the cable at the arterial side while the delivery sheath of the MVTD is set among the rollers at the that will cause the MVTD to be pushed forward at the venous side at the same rate, causing the MVTD to move toward the mitral valve position. Such a system might employ a wired or wireless user controller. The controller can include a first input (e.g. a button, slider, etc) used to selectively cause movement (pulling or pushing force) at the arterial side and a second input used to selectively cause equal pulling and pushing forces at the venous side in a reverse direction. The controller preferably includes "dead man" switches, so that all motion stops instantly if either button is released. (The controller might also include a single input or mode of operation that causes the drive unit to simultaneously pull the cable and push the MVTD at the same rate.) A third input is used to cause an increased rate of movement in the pull direction to be greater than the rate of movement in the pull direction in order to steer the tip of the MVTD down and to the patient's left when traversing the interatrial septum and left atrium. A fourth input can be employed to cause more push than pulling force in order to drive the segmental tensioner harder into the protective sleeve of the steering section of the LVR in order to keep it pushed into the LV apex during increased tension on the cable during transit of the MVTD.

The disclosed system and method are described here as "guidewireless" because the step of moving the MVTD into position across the mitral valve site is performed without guidewires. Note that other steps may utilize guidewires without departing from the scope of the invention. As a non-limiting example, should the practitioner observe the tracker catheter heading off course as it approaches the aorta, a guidewire may be introduced via the arterial side into the distal lumen opening at the balloon catheter tip so that the tracker balloon catheter can track over the guidewire to the target vessel in the arterial vasculature All patents and patent applications referred to herein, including for purposes of priority, are fully incorporated herein by reference.

We claim:

1. A method of delivering a therapeutic device to a target treatment site at a valve annulus in a heart of a patient, comprising the steps of:
   (a) percutaneously introducing a cable into a vasculature of a patient and positioning the cable to run from a femoral vein, through the heart via a transseptal puncture, and to a femoral artery, such that a first end of the cable is exposed from the femoral vein and a second end, opposite the first end, of the cable is exposed from the femoral artery;
   (b) at the femoral artery, securing the therapeutic device to the cable, the therapeutic device comprising a heart valve delivery device carrying a replacement valve;
   (c) providing a left ventricle redirector (LVR) having a tubular lumen, advancing a distal end of the lumen over the cable at the femoral vein and advancing the LVR to the left ventricle;
   (d) pulling the cable at the femoral vein while pushing the therapeutic device at the femoral artery to advance the therapeutic device to the target treatment site;
   (e) during step (d), actively steering the distal end of the LVR, said steering modifying an orientation of a distal nose of the therapeutic device; and
   (f) deploying the replacement valve at the valve annulus.

2. The method of claim 1, further including:
   engaging a distal part of the therapeutic device with the distal end of the LVR;
   actively steering the distal end of the LVR to form a curve in the distal end of the LVR;
   seating an edge of the curve of the LVR within the apex of the left ventricle; and
   during step (d), applying a force to the LVR in a distal direction to press the curve into the apex of the left ventricle.

3. The method of claim 2, wherein applying the force to the LVR orients the distal nose of the therapeutic device inferiorly and towards the patient's left side.

4. The method of claim 2, wherein applying the force to the LVR prevents migration of the LVR into the valve leaflets.

5. The method of claim 2, wherein engaging the distal part of the therapeutic device with the distal end of the LVR includes:
   providing a tubular connector having a distal end and a proximal end;
   in step (b), inserting the distal nose of the therapeutic device into the proximal end of the tubular connector;
   in step (d) causing the distal end of the tubular connector to pass into the distal end of the LVR.

6. The method of claim 5, further including centering the therapeutic device within the valve annulus using any combination of torquing the LVR, advancing or retracting the LVR in a proximal or distal direction, or actively modifying tension on a pullwire used to actively steer the curve of the LVR.

7. The method of claim 1, wherein step (a) includes:
   positioning an expandable tip of a balloon catheter in the right atrium and passing the tip through the interatrial septum into the left atrium, the balloon catheter having a balloon at its distal end;
   inflating the balloon, causing the balloon catheter to be carried by blood flow into and through the aorta to the femoral artery;
   introducing a right-to-left conduit (RLC) over a proximal end of the balloon catheter;
   advancing the RLC over the balloon catheter to position a distal end of the RLC proximate to an incision in the left femoral artery;
   introducing the second end of the cable into the RLC at the femoral vein, and advancing the second end of the cable to the distal end of the RLC;
   capturing the second end of the cable via the femoral artery and positioning the second end external to the body.

8. The method of claim 7, wherein the step of capturing the second end includes advancing a snare into the vasculature via the left femoral artery and engaging the second end of the cable using the snare.

9. The method of claim 1 wherein the femoral vein is the right femoral vein and the femoral artery is the left femoral artery.

10. The method of claim 1 wherein the femoral vein is the right femoral vein and the femoral artery is the right femoral artery.

11. The method of claim 1, wherein the valve annulus is a mitral valve annulus.

12. The method of claim 1, wherein step (e) comprises forming a curve in the distal end of the LVR and actively modifying tension on a pullwire used to actively steer the curve of the LVR.

13. The method of claim 12, wherein the pullwire includes a distal section extending external to the LVR, and wherein actively steering the curve of the LVR causes the distal end of the tubular lumen and the distal section of the pullwire to form a generally D-shaped arrangement.

* * * * *